United States Patent [19]

Tarzia et al.

[11] 3,993,650
[45] Nov. 23, 1976

[54] PYRROLO [3,4-d] PYRIMIDINES

[75] Inventors: Giorgio Tarzia, Rome; Gianbattista Panzone, Cornaredo (Milan), both of Italy

[73] Assignee: Gruppo Lepetit S.p.A., Milan, Italy

[22] Filed: Mar. 17, 1975

[21] Appl. No.: 559,091

[30] Foreign Application Priority Data

Mar. 20, 1975 United Kingdom............... 12387/74

[52] U.S. Cl.................... 260/256.4 F; 260/256.4 B; 424/251
[51] Int. Cl.²........................ C07D 487/04
[58] Field of Search............... 260/256.4 F

[56] References Cited
UNITED STATES PATENTS 3,769,288  11/1973  Stahle et al................... 260/256.4 F
3,853,898  12/1974  Hardtmann et al........... 260/256.4 F

OTHER PUBLICATIONS

Brown, *Heterocyclic Compounds: Fused Pyrimidines,* Part I, 1967, Interscience Publishers, New York, pp. 120–122.

*Primary Examiner*—Nicholas S. Rizzo
*Assistant Examiner*—James H. Turnipseed
*Attorney, Agent, or Firm*—Theodore Post; C. Kenneth Bjork

[57] ABSTRACT

Pyrrolo [3,4-d] pyrimidines of the following formula:

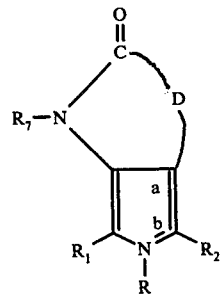

The compounds have anti-inflammatory and prostaglandin synthetase inhibitory utility.

1 Claim, No Drawings

PYRROLO [3,4-D] PYRIMIDINES

The present invention relates to new heterocyclic compounds with pharmacological activity, of the following general formula

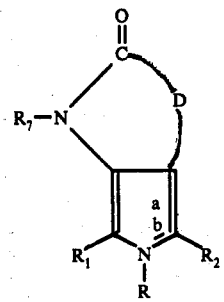

I wherein:
- R represents hydrogen, ($C_{1-4}$) alkyl, e.g. methyl, ethyl, isopropyl, butyl, isobutyl or tert-butyl, or nil;
- $R_1$ stands for hydrogen, phenyl or phenyl substituted with methyl, ethyl, methoxy, hydroxy, fluoro, chloro or bromo such as, for instance, p-tolyl, o-tolyl, p-anisyl, m-hydroxy phenyl, p-hydroxyphenyl, p-chlorophenyl, o-chlorophenyl, p-fluorophenyl or m-bromophenyl;
- $R_2$ is selected from hydrogen, ($C_{1-4}$) alkyl as above defined, phenyl, carbo ($C_{1-3}$) alkoxy e.g. carbomethoxy, carbethoxy, carbopropoxy or carboisopropoxy, and carboxy;
- $R_7$ represents hydrogen, ($C_{1-4}$) alkyl as above defined, benzyl or halo-substituted benzyl, e.g. p-chlorobenzyl o-chlorobenzyl, p-fluorobenzyl or m-bromobenzyl;
- D is a radical selected from the groups

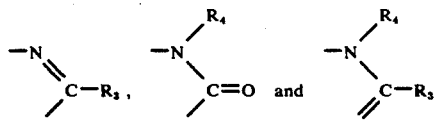

whose carbon atoms are linked to the carbon atoms of the pyrrole nucleus, and wherein $R_3$ represents ($C_{1-4}$) alkyl as above defined or phenyl, and $R_4$ represents hydrogen ($C_{1-4}$) alkyl as above defined or phenyl; the signatures -a- and -b- represent nil or an additional bond, though not simultaneously nil or an additional bond, with the proviso that, when D is selected from

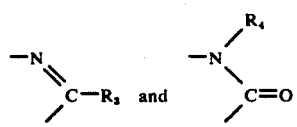

,—a— is an additional bond, —b— represents nil, and R is hydrogen or ($C_{1-4}$) alkyl as above defined, with the further proviso that, when D represents the group

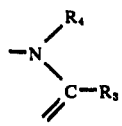

—a— and R represents nil and —b— is an additional bond; and to salts therewith of pharmaceutically acceptable acids. In numbering the substances of the formula I above, the rules of the I.U.P.A.C. have been followed. For the sake of better understanding, the basic skeleton ring can be named pyrrolo [3,4-d] pyrimidine and the various positions are numbered as indicated below

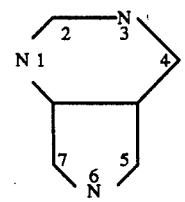

Considering the nature of the various substituents, it is understandable to any person who is skilled in the art that the compounds of the above formula I may exist in several different tautomeric forms: said forms are in a state of dynamic equilibrium ie,. they rapidly exchange into each other and are in any case considered as a part of the invention. As an example, when $R_7$ is hydrogen and/or D is the group

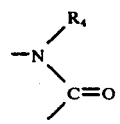

in which $R_4$ is hydrogen, the compounds of the above formula I, which are in the keto-form, may exist also as the corresponding enolic tautomers (see in this connection, R. C. Elderfield, Heterocyclic Compounds, Vol. 6, pages 257–58, John Wiley and Sons Inc. New York 1957). The process for preparing the compounds of the invention comprises reacting a β-aminopyrrole derivative of the formula

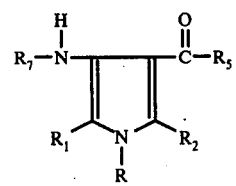

II or an acid addition salt thereof, wherein R, $R_2$ and $R_7$ have the above meanings and $R_5$ is selected from an alkoxy group of from 1 to 3 carbon atoms, ($C_{1-4}$) alkyl as above defined and phenyl, with a compound of the formula

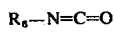   III wherein $R_6$ may represent hydrogen, an alkali metal, ($C_{1-4}$) alkyl as above defined, or phenyl.

According to a preferred embodiment of the present invention, the reaction is performed by mixing the two reactants of the above formulas II and III, in the presence of a suitable solvent in substantially equimolecular ratios, though a slight excess of the compound of formula III may be sometimes desirable in order to have a more favorable reaction course. The presence of an acidic solvent is required when $R_6$ is an alkali metal : many organic and inorganic acids or their mixtures with water can suitably be utilised for this purpose and it has been found that the best results are obtained with mixtures of water and acetic acid. On the other hand, if the starting substances of formula II are employed as the corresponding acid salts, an amount of a tertiary organic nitrogen containing base is conveniently added to the reaction mixture, in order to block the acid which forms during the course of the reaction itself. For this purpose it has been found that triethylamine, pyridine, quinoline, isoquinoline or their methyl homologs can suitably be employed and in many instances they also act as the reaction solvents. The reaction generally occurs at room temperature and is completed within about 30 minutes – 2 hours.

An open intermediate compound of formula IV forms

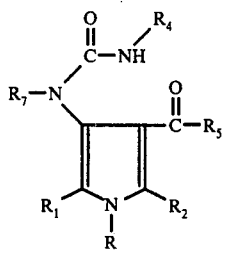   IV wherein R, $R_1$, $R_2$, $R_3$, $R_4$, $R_5$, and $R_7$, have the meanings given above, which in many cases has been isolated and characterized.

However, the above compound of formula IV may be used as a raw material for the subsequent cyclization step without affecting the final yields. Accordingly, it is cyclized to the desired end product of formula I by means of cycling agents such as, for instance, hydroxides, carbonates or alkoxides of alkali metals. Said cyclizing agents are added in at least one molar proportion over the starting material of formula II. The reaction is carried out at a temperature ranging from room temperature to the boiling temperature of the reaction mixture and is completed within about 30 minutes – 2 hours. The compounds of formula I may be recovered from the reaction medium as free bases or as the corresponding salts of pharmaceutically acceptable acids, following techniques which are entirely familiar to a skilled chemist. For instance, they can suitably be recovered by filtration being high-melting solids, and, if necessary purified by column chromatography or recrystallization from organic solvents.

The foregoing mentioned salts of pharmaceutically acceptable acids are essentially represented by the hydrochloride, hydrobromide, hydroiodide, sulfate, phosphate, benzoate, oxalate, acetate, methanesulfonate, cyclohexylsulfonate, and analogs. These salts possess the same degree of activity of the free bases, and accordingly, they are included within the scopes of the present invention. They are easily obtained by treating a compound of formula I as the free base with the predetermined pharmaceutically acceptable acid. In turn, it is possible to restore the free base from the corresponding salt by reaction with at least one equimolecular amount of a basic agent.

The nature of the end products depends on the starting substrate of formula II. More exactly, compounds of formula I wherein D represents the radical

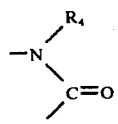

are obtained when $R_5$ represents an alkoxy group of 1 to 3 carbon atoms, compounds of formula I wherein D is the group

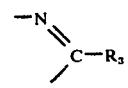

or the group

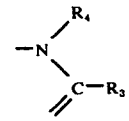

are obtained when $R_5$ represents ($C_{1-4}$) alkyl as above defined on phenyl. The starting compounds of formula III are commercially available products. The starting substances of formula II are prepared through a process which involves the reaction between an α-aminonitrile of formula

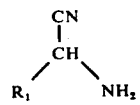

and a β-dicarbonyl compound of formula

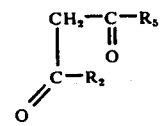

wherein $R_1$, $R_2$ and $R_5$ have the aforesaid meanings. The formed β-aminopyrrole of formula

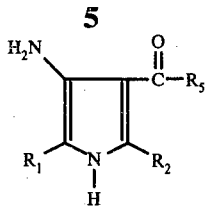

corresponding to the compound of formula II wherein R and R₇ both represent hydrogen can then be transformed by common chemical procedures into the other desired starting materials of formula II.

Also the compounds of formula I obtained through the process of the present invention may undergo subsequent chemical modifications, according to which it is possible to transform an already preexisting radical into another group falling within the general meanings given the substituents on the pyrrolo [3,4-d] pyrimidine nucleus.

For instance, when $R_2$ in the above formula I represents a carbo($C_{1-3}$) alkoxy group, a simple hydrolysis performed according to known procedures for hydrolizing esters gives the corresponding 5-carboxy derivative. Other obvious procedures capable of transforming a substituent into another falling within the meanings given before, are considered as a part of the invention.

The compounds of the invention display excellent pharmacological properties; more particularly they are active essentially as antiinflammatories and as prostaglandin synthetase inhibitors. The antiinflammatory activity was investigated through the "carragenin induced edema" test in rats, which was performed following substantially the operative schema proposed by C.A. Winter et al. in Proc. Soc. Expl. Biol. Med., 111, 544, 1962.

Representative experiments showed that dose levels ranging from about 20 to about 50 mg/kg per os of the compounds of examples 3, 6 and 7 caused a decrease of the induced edema in the laboratory animals of at least 30% over the controls ie., the animals in which an edema was induced but which did not receive the substance to be investigated. It must be noted that a percent decrease of the edema of 30 is absolutely significative from the pharmacological standpoint. Moreover when administered per os at 100 mg/kg the compounds of examples 3 and 7 caused a decrease of the induced edema of about 55%. These very favorable antiinflammatory properties are coupled with a low toxicity, being the $LD_{50}$ of the compounds of the invention always higher than 500 mg/kg p.o. in mice. Toxicities were determined substantially according to the method described by Lichtfield and Wilcoxon in Journ. Pharm. Expt. Ther., 96, 99 1949.

Finally some of the compounds of the invention display interesting C.N.S. depressant properties and possess a valuable degree of activity on the hydric balance of warm blooded animals. The compounds of the invention may be administered by various routes. While the preferred routes of administration are oral and rectal, parenteral administration can also be employed. For oral administration, the compounds are compounded into pharmaceutical dosage forms, such as, for instance, tablets, capsules, elixiris, solutions and the like. The dosage unit may contain the usual excipients, e.g. starch, gums, fatty acids, alcohols, sugars, etc. For rectal administration the compounds are administered in the form of suppositories, admixed with conventional vehicles, such as, for example, cocoa butter, wax, spermaceti or polyoxyethyleneglycols and their derivatives. The dosage range is from about 0.05 to about 2.00 g. per day, preferably administered in divided dose.

Accordingly the present invention provides a therapeutic composition comprising as the active ingredient a compound of the invention together with a pharmaceutically acceptable carrier.

The following additional description and examples further describe the invention and the manner and process of making and using it to enable the art skilled to make and use the same and set forth the best mode contemplated by inventors of carrying out the invention.

EXAMPLE 1

4,5-Dimethyl-7-phenyl-6H-pyrrolo [3,4-d]pyrimidine-2-(1H)-one.

A. To a solution of 8.0 g. (0.0374 mole) of 4-acetyl-3-amino-5-methyl-2-phenyl-pyrrole in 60 ml. of acetic acid, a solution of 2.5 g. (0.0374 mole) of sodium isocyanate in 30 ml. of water is added at room temperature under stirring. Stirring is continued for 30 minutes, than the reaction mixture is allowed to stand for 1 hour. A solid precipitates, which is recovered by filtration and recrystallized from acetone/hexane. Yield 11.0 g. M.p. 234°–8° C. This compound is the open intermediate of the formula IV 4-acetyl-5-methyl-2-phenyl-3-ureido-pyrrole.

B. 3.0 Grams (0.0117 mole) of the compound prepared under A are dissolved in 160 ml. of anhydrous methanol, then a solution resulting from 0.3 g. of sodium in 120 ml. of anhydrous methanol is added dropwise at room temperature. The resulting mixture is refluxed for 30 minutes and then allowed to stand for 1 hour. A solid precipitate forms, which is recovered by filtration and washed with water. Yield 1.4 g. of the title compound, which needs no further purification. M.p. 290°–4° C.

By operating substantially as described in example 1, and isolating if desired, the open intermediate compound of the formula IV, the following compounds have been prepared. When nothing is said in the examples about the intermediate compounds, it is intended that they have not been isolated.

EXAMPLES 2–10

2. 5-Methyl-4,7-diphenyl-6H-pyrrolo[3,4-d]pyrimidine-2(1H)-one, from 3-amino-4-benzoyl-5-methyl-2-phenyl-pyrrole and sodium isocyanate. Yield 71,4% M.p. 330° C (decomposition).

3. 3-Ethyl-5-methyl-4,7-diphenyl-1H-pyrrolo[3,4-d]pyrimidine-2(3H)-one hydrochloride, from 3-amino-4-benzoyl-5-methyl 2-phenyl-pyrrole and ethylisocyanate. Yield 77%. M.p. 331°–32° C. (from methanol/water).

4. 5-Methyl-4-phenyl-6H-pyrrolo[3,4-d]pyrimidine-2(1H)-one, from 3-amino-4-benzoyl-5-methyl-pyrrole hydrochloride and sodium isocyanate. The intermediate compounds melts at 230° C. Yield of the title compound:67% M.p. 330° C(dec.) (from ethanol/water)

5. 1-Ethyl-5-methyl-4,7-diphenyl-6H-pyrrolo[3,4-d]pyrimidine-2(1H)-one, from 4-benzoyl-3-ethylamino-5-methyl-2-phenyl-pyrrole and sodium isocyanate. Yield 71%. M.p. 323°–25° C.(from ethanol/water).

6. 6-Ethyl-5-methyl-4,7-diphenyl-6H-pyrrolo[3,4-d]pyrimidine-2(1H)-one, from 3-amino-4-benzoyl-1- ethyl-5-methyl-2-phenylpyrrole hydrochloride and sodium isocyanate. Yield 74%. M.p. 240°–42° C. (from ethylacetate).

7. 1,6-Diethyl-5-methyl-4,7-diphenyl-6H-pyrrolo[3,4-d]pyrimidine-2(1H)-one, from 4-benzoyl-1-ethyl-3-ethylamino-5-methyl-2-phenylpyrrole and sodium isocyanate. Yield 66%. M.p. 197°–98° C (from methanol).

8. 1-Isopropyl-5-methyl-4,7-diphenyl-6H-pyrrolo[3,4-d]pyrimidine-2(1H)-one, from 4-benzoyl-3-isopropylamino-5-methyl-2-phenyl-pyrrole and sodium isocyanate. M.p. 350°–53° C.(from methanol/water).

9. 6-Butyl-4,5-dimethyl-7-(p-tolyl)-6H-pyrrolo[3,4-d]pyrimidine-2(1H)-one, from 4-acetyl-3-amino-1-butyl-5-methyl-2-(p-tolyl) pyrrole-hydrochloride and sodium isocyanate. Yield 81%. M.p. 203°–4° C. (from ethanol).

10. 1-(p-Chlorobenzyl)-4,5-dimethyl-7-(o-tolyl)-6H-pyrrolo [3,4-d]pyrimidine-2(1H)-one, from 4-acetyl-3-(p-chlorobenzyl)-amino-5-methyl-2-(o-tolyl)-pyrrole and sodium isocyanate. Yield 62%. M.p. 337°–39° C. (from methanol/water).

EXAMPLE 11

5-Methyl-3,7-diphenyl-6H-pyrrolo[3,4-d]pyrimidine-2,4(1H,3H) dione.

A. To a solution of 10 g. (0.041 mole) of 3-amino-4-carbethoxy-5-methyl-2-phenyl-pyrrole hydrochloride in 100 ml. of pyridine 6 g. (0.0504 mole) of phenyl isocyanate are added at room temperature and the resulting mixture is stirred for 2 hours. Then the whole is poured into hydrochloric acid/water and the solid precipitate which forms is recrystallized from a mixture of ethanol/water. Yield 16.9 g. M.p. 224°–6° C. This compound corresponds to the open intermediate of the formula IV wherein R and $R_7$ are hydrogen, $R_1$ and $R_4$ are phenyl, $R_5$ is ethoxy and $R_2$ is methyl.

B. To a solution obtained from 0.5 g. of sodium in 50 ml. of anhydrous ethanol a solution of 3 g. (0.0826 mole) of the compound prepared under A in 200 ml. of anhydrous ethanol is added. The mixture is refluxed for 5 hours, then cooled and poured into a saturated aqueos solution of NaCl. The title compound precipitates, which is recovered by filtration and recrystallized from ethanol. Yield 2 g.. The compound does not melt up to 350° C and contains half a molecule of water. By operating substantially as described in example 12, the following compounds have been prepared. When nothing is said in the example about the intermediate compounds of formula IV, it is intended that they have not been isolated.

EXAMPLES 12–15

12. 5-Methyl-7-phenyl-6H-pyrrolo[3,4-d]pyrimidine-2,4(1H,3H)-dione, from 3-amino-4-carbethoxy-5-methyl-2-phenyl-pyrrole hydrochloride and sodium isocyanate.

The intermediate compound melts at 217°–19° C (from ethanol). Yield of the title compound 79%. M.p. 292°–3° C. (from methanol).

13. 3,5-dimethyl-7phenyl-6H-pyrrole[3,4-d]pyrimidine-2,4(1H,3H)-dione, from 3-amino-4-carbethoxy-5-methyl-2-phenyl-pyrrole hydrochloride and methylisocyanate. Yield 80% M.p. 344°–47° C (from ethanol/water).

14. 6-Butyl-5-methyl-7-phenyl-6H-pyrrolo[3,4-d]pyrimidine-2,4(1H,3H)-dione, from 3-amino-1-butyl-4-carbomethoxy-5-methyl-2-phenyl-pyrrole hydrochloride and sodium isocyanate. Yield 76%. M.p. 227°–28° C (from methanol/water).

15. 5-Carbomethoxy-7-phenyl-6H-pyrrolo[3,4-d]pyrimidine-2,4(1H,3H)-dione, from 3-amino-4,5-dicarbomethoxy-2-phenyl-pyrrole and sodium isocyanate. The intermediate 4,5-dicarbomethoxy-2-phenyl-3-ureido-pyrrole is isolated. M.p. 246°–8° C (from methanol/water). Yield of the title compound 88.5%. M.p. 320°–7° C. (from methanol/water).

EXAMPLE 16

5-Carboxy-7-phenyl-6H-pyrrolo [3,4-d]pyrimidine-2,4(1H,3H)-dione. 3 Grams (0.0105 mole) of the compound of the example 3 are suspended in 50 ml. of ethanol and 50 ml. of aqueos 25% sodium hydroxide and the resulting mixture is refluxed for 3 hours. After cooling the reaction solution is poured into a medium consisting of 100 g. of crushed ice and 150 ml. of aqueos 10% hydrochloric acid. The title compound precipitates and is recovered by filtration. Yield 2.4 g. The compound does not melt up to 360° C.

Typical compounds which can be prepared pursuant to the procedure outlined in the above reported examples are:

5-Ethyl-4,7-diphenyl-6H-pyrrolo[3,4-d]pyrimidine-2(1H)-one

5-Methyl-4,6-dipropyl-7-(p-tolyl)-6H-pyrrolo[3,4-d]-pyrimidine-2(1H)-one 7-(p-Anisyl)-5-butyl-4-phenyl-6H-pyrrolo [3,4-d]pyrimidine-2(1H)-one 5-Carbomethoxy-1-ethyl-7-(p-hydroxyphenyl)-4-methyl-6H-pyrrolo [3,4-d]pyrimidine-2)1H)-one 6-Butyl-4,5-diphenyl-6H-pyrrolo[3,4-d]pyrimidine-2(1H)-one 1,6-Diisopropyl-4,7-diphenyl-5-methyl-6H-pyrrolo[3,4-d]pyrimidine-2(1H)-one 5-Butyl-7-(p-chlorophenyl)-6-methyl-6H-pyrrolo[3,4-d]pyrimidine-2,4(1H,3H)-dione 7-(m-Chlorophenyl)-3,5-diphenyl-6H-pyrrolo[3,4-d]pyrimidine-2,4-(1H,3H)-dione 3-Butyl-4-ethyl-5-methyl-7-(p-tolyl)-6H-pyrrolo[3,4-d]pyrimidine-2,4(1H,3H)-dione 6-Butyl-5-ethyl-3-methyl-7-phenyl-6H-pyrrolo[3,4-d]pyrimidine-2,4(1H,3H)-dione 4-Isopropyl-5-methyl-3,7-diphenyl-1H-pyrrolo[3,4-d]pyrimidine-2(3H)-one 7-(p-Chlorophenyl)-1-isopropyl-5-methyl-3,4-diphenyl-1H-pyrrolo[3,4-d]pyrimidine-2(3H)-one hydrochloride 7-(o-Anisyl)-1,3,4-triethyl-5-phenyl-1H-pyrrolo[3,4-d]pyrimidine-2(3H)-one 3,5-Diethyl-4-isobutyl-7-phenyl-1H-pyrrolo[3,4-d]pyrimidine-2(3H)-one 4,5-Dimethyl-3,7-diphenyl-1H-pyrrolo[3,4-d]pyrimidine-2(3H)-one hydrochloride Preparation of the starting β-aminopyrroles of formula II A) 4-Acetyl-3-amino-5-methyl-2-phenyl-pyrrole a. A solution of 2 g. (0.015 mole) of 2-amino-2-phenylacetonitrile and 1.4 g. (0.014 mole) of acetylacetone in 30 ml. of anhydrous benzene is refluxed for two hours on an oil bath in the presence of 100 mg. of p-toluenesulfonic acid. After cooling, the reaction mixture is filtered, then the solvent is evaporated off to give an oily residue which is distilled under reduced pressure; the fraction boiling at 150° C./0.1 mmHg is collected.

b. 0.40 Grams of sodium are dissolved in 15 ml. of anhydrous ethanol, then a solution of 2.5 g. of the fraction boiling at 150° C./0.1 mmHg prepared as in point (a) in anhydrous ethanol is added dropwise and the mixture is allowed to stand at room temperature for 4 hours. After bubbling hydrogen chloride in the ethanol solution, a precipitate forms, which is recovered by filtration and recrystallized from ethanol/diethyl ether. Yield 2.0 g. of the title compound as the corresponding hydrochloride, which melts at 242° C (with decomposition). The title compound is obtained by extraction with ethyl acetate of an aqueos solution of the hydrochloride alkalinized with 5% sodium hydroxide. M.p. 220° C. (from methanol).

According to the procedure described in the previous example the following starting compounds of formula II have been prepared

| Compound | M.p. ° C |
|---|---|
| B) 3-Amino-4-benzoyl-5-methyl-2-phenyl-pyrrole | 203–5 |
| C) 3-Amino-4-benzoyl-2-phenyl-pyrrole hydrochloride | 272–74 |
| D) 3-Amino-4-carbethoxy-5-methyl-pyrrole hydrochloride | 249–52 |
| E) 3-Amino-4,5-dicarbomethoxy-2-phenyl-pyrrole | 142–43 |

Preparation of

F. 4-Benzoyl-3-ethylamino-5-methyl-2-phenyl-pyrrole

This compound is prepared from compound B) which is transformed into the corresponding 3-(p-toluenesulfonamido)-derivative (M.p. 230°–33° C). By reaction with diethylsulfate one obtains 4-benzoyl-3-(N-ethyl-p-toluenesulfonamido)-5-methyl-2-phenyl-pyrrole (M.p. 224°–25° C), which is converted into the title compound by acid hydrolysis. M.p. of the title compound 178°–80° C. Preparation of G) 4-benzoyl-3-isopropylamino-5-methyl-2-phenyl-pyrrole This compound is prepared from compound B) and isopropyl bromide M.p. 132°–36° C. Preparation of 4) 3-Amino-4-benzoyl-1-ethyl-5-methyl-2-phenyl-pyrrole The synthesis of this compound starts from compound (B) which is reacted with benzaldehyde to the corresponding Schiff's base. This product is subsequently treated with sodium hydride and then with ethyliodide, whereby 3-benzylideneamino-4-benzoyl-1-ethyl-5-methyl-2-phenyl-pyrrole (M.p. 147°–48° C) is obtained. This compound is then hydrolized in mild acidic conditions to the title substance (M.p. 238°–40° C).

The following compound have been prepared pursuant to the same procedure of the previous example. The melting points of the starting β-aminopyrroles, if necessary, are reported: they have been prepared substantially as described for synthesis of compound A).

I) 4-acetyl-3-amino-1-butyl-5-methyl-2-(p-tolyl)-pyrrole, from 4-acetyl-3-amino-5-methyl-2-(p-tolyl)-pyrrole (M.p. 232°–34° C). M.p. of the title compound 93°–94° C.

J. 3-Amino-1-butyl-4-carbethoxy-5-methyl-2-phenyl-pyrrole hydrochloride, from compound D) M.p. of the title compound 189°–92° C.

Preparation of

K. 4-Benzoyl-1-ethyl-3-ethylamino-5-methyl-2-phenyl-pyrrole

Compound B) is transformed into the corresponding p-toluene sulfonamido derivative (M.p. 230°–33° C) by reaction with p-toluenesulfonychloride. This compound is subsequently reacted in strong alkaline solution with diethylsulfate, thus obtaining 4-benzoyl-3-(N-ethyl-p-toluenesulfonamido)-5-methyl-2-phenyl-pyrrole (M.p. 152°–53° C), which is in turn converted into the title compound (B.p. 220° C/0.015 mmHg) by acid hydrolysis.

Preparation of

L. 4-acetyl-3-(p-chlorobenzylamino)-5-methyl-2-(o-tolyl)-pyrrole

The title compound (M.p. 167°–70° C) is prepared from 4-acetyl-3-amino-5-methyl-2-(o-tolyl)-pyrrole (m.p. 258° C), obtained substantially in the same way as compound A), by transforming into the corresponding p-chlorobenzylidene derivative (m.p. 215° C) by reaction with p-chlorobenzaldehyde and subsequent catalytic hydrogenation.

I claim:

1. A compound of the formula

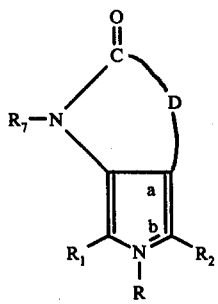

wherein:

R is hydrogen, ($C_{1-4}$) alkyl or nil;

$R_1$ is hydrogen, phenyl or phenyl substituted with methyl, ethyl, methoxy, hydroxy, fluoro, chloro or bromo;

$R_2$ is hydrogen, ($C_{1-4}$) alkyl, phenyl, carbo ($C_{1-3}$) alkoxy, or carboxy;

$R_7$ is hydrogen ($C_{1-4}$) alkyl, benzyl or halo-substituted benzyl;

D is

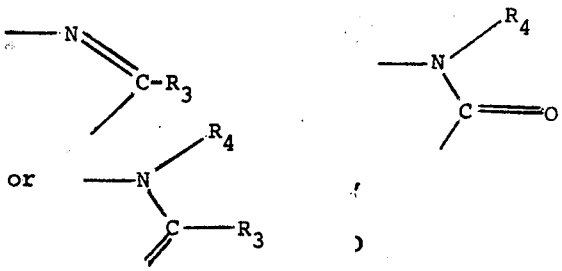

whose carbon atoms are linked to the carbon atoms of the pyrrole nucleus, and wherein $R_3$ is $(C_{1-4})$ alkyl or phenyl, and $R_4$ is hydrogen, $(C_{1-4})$ alkyl or phenyl;

the signatures —a— and —b— represent nil or an additional bond, though not simultaneously nil or an additional bond, with the proviso that, when D is

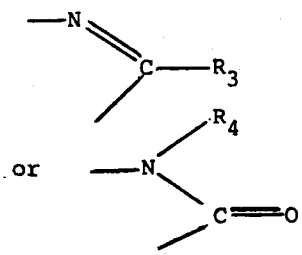

—a— is an additional bond, —b— represents nil, and R is hydrogen or $(C_{1-4})$ alkyl, with the further proviso that, when D represents the group

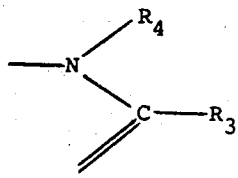

—a— and R represent nil and —b— is an additional bond;

and a salt thereof with a pharmaceutically acceptable acid.

* * * * *